United States Patent
Ibrahim et al.

(10) Patent No.: US 7,070,796 B1
(45) Date of Patent: Jul. 4, 2006

(54) PHARMACEUTICALLY STABLE OXALIPLATINUM PREPARATION FOR PARENTERAL ADMINISTRATION

(75) Inventors: Houssam Ibrahim, Veyrier (CH); Martine Bayssas, Lausanne (CH); Henri Pourrat, Clermont-Ferrand (FR); Christine Deuschel, Trélex (CH)

(73) Assignee: Debiopharm S.A., Lausanne (CH)

( * ) Notice: Subject to any disclaimer, the term of this patent is extended or adjusted under 35 U.S.C. 154(b) by 516 days.

(21) Appl. No.: 10/049,379

(22) PCT Filed: Aug. 30, 2000

(86) PCT No.: PCT/CH00/00462

§ 371 (c)(1),
(2), (4) Date: Feb. 12, 2002

(87) PCT Pub. No.: WO01/15691

PCT Pub. Date: Mar. 8, 2001

Related U.S. Application Data

(60) Provisional application No. 60/151,357, filed on Aug. 30, 1999.

(51) Int. Cl.
*A61F 13/00* (2006.01)
*A61F 2/00* (2006.01)
*A61K 9/00* (2006.01)

(52) U.S. Cl. .................. 424/422; 424/400; 424/423

(58) Field of Classification Search ................ 424/400, 424/422, 423
See application file for complete search history.

(56) References Cited

U.S. PATENT DOCUMENTS

| 4,439,181 A | * | 3/1984 | Blackshear et al. | 604/518 |
| 5,716,988 A | * | 2/1998 | Ibrahim et al. | 514/492 |
| 5,897,871 A | * | 4/1999 | Schlipalius | 424/423 |

FOREIGN PATENT DOCUMENTS

| WO | WO 94/12193 | 6/1994 |
| WO | WO 96/04904 | 2/1996 |
| WO | WO 98/39009 | 9/1998 |
| WO | WO 99/43355 | 9/1999 |

* cited by examiner

*Primary Examiner*—Humera N. Sheikh
(74) *Attorney, Agent, or Firm*—Nixon & Vanderhye P.C.

(57) ABSTRACT

The invention concerns a pharmaceutically stable oxaliplatinum preparation for parenteral administration, the oxaliplatinum being in a precipitate-free, colorless and clear solution after being preserved for a pharmaceutical acceptable duration. In said preparation, the oxaliplatinum is contained in a solution in a solvent at a concentration of at least 7 mg/ml and the solvent comprises a sufficient amount of at least a hydroxylated derivative selected among 1,2-propane-diol, glycerol, maltitol, saccharose and inositol. The invention also concerns a method for preparing said solution.

14 Claims, No Drawings

PHARMACEUTICALLY STABLE OXALIPLATINUM PREPARATION FOR PARENTERAL ADMINISTRATION

This application is the U.S. national phase of international application PCT/CH00/00462 filed Aug. 30, 2000 which claims the benefit of Provisional application Ser. No. 60/151,357, filed Aug. 30, 1999, which designated the U.S.

The present invention concerns a pharmaceutically stable oxaliplatinum preparation for parenteral administration intended to be perfused or injected, the oxaliplatinum being in a precipitate-free, colorless and clear solution after being preserved for a pharmaceutical acceptable duration at temperatures going from 2° C. to 30° C. The invention also concerns a method for preparing said solution.

The oxaliplatinum (INN, also called/-OHP), complex derivative of platinum (CAS RN: 61825-94-3) described by Kidani and al. in J. Med. Chem., 1978, 21, 1315, is a antineoplastic agent used per intravenous administration in particular in the treatment of metastatic colorectal cancers. Today, it is used in hospitals in a lyophilized form and its liquid preparation is reconstituted with help of a glucosed solution just before its administration, generally a short duration perfusion.

The oxaliplatinum, in this lyophilized form, is formulated with a large amount of lactose (of a factor 9 in weight relative to the oxaliplatinum). It is then a powder or a cake of whitish color. During its reconstitution, it is recommended to use a quantity of glucosed solution so that the concentration of oxaliplastinum in the obtained preparation is comprised between 2,5 and 5,0 mg/ml.

The oxaliplatinum, in form of a pure active substance, is known to be slightly soluble in water, very little soluble in methanol and practically insoluble in ethanol and acetone. More precisely, the maximal solubility of oxaliplatinum saturated in water at 37° C. is of 7,9 mg/ml, but at 20° C. it falls down to 6 mg/ml. In methanol at 20° C., it is only of 0,22 mg/ml.

Recently, a pharmaceutically stable oxaliplatinum preparation, ready to be administrated parenterally by perfusion, constituted by an aqueous solution of oxaliplatinum at a concentration of about 2 mg/ml, and not containing other adjuvants, has been described by Ibrahim and al. in WO 96/04904.

This preparation offered to the hospital staff the great advantage, on one side, avoiding the manipulation of a cytotoxic powder or cake during the reconstitution of the pharmaceutical preparation and, on the other hand, avoiding the risk to use by mistake a reconstitution solution containing chloride ions, such as a sodium chloride solution usually used in this kind of operations, which has the terrible consequence to decompose the metallic complex.

On the other hand, this preparation was not satisfactory, in particular, because of its oxaliplatinum concentration which was much lower than the solubilities mentioned above. This low concentration is required to prevent all risk of precipitates or crystals susceptible to appear, for example, during conservation at low temperatures in a refrigerator or during transport at winter conditions. When such precipitates appear in a pharmaceutical preparation, the hospital staff is generally warned, if there is a doubt, to keep this sample out. If however, a redissolution should be attempted, a heating process at temperatures higher than 40° C., possibly coupled with sonication should be done.

This is why a pharmaceutical preparation based on an oxaliplatinum solution at a concentration of 2 mg/ml, as described in WO 96/04904, needs manipulation of big volumes. For example, the generally recommended dosage during a short perfusion treatment of between 2 and 6 hours, is of 130 mg oxaliplatinum per $m^2$ body surface. When taking an average body surface of 1,7 $m^2$, it is then advisable to use at least 110 ml of this 2 mg/ml preparation.

One of the aims of the present invention is to make available a stable oxaliplatinum pharmaceutical preparation, for parenteral administration intended to be perfused of injected, in which the oxaliplatinum concentration would be clearly increased in a way to significantly reduce the volumes to manipulate and/or to use.

With such preparations, it will then be possible to further facilitate the work of the hospital staff while improving their security.

Indeed, the number of flasks, or their volume, will be lower, thus reducing the risk when a bad manipulation would lead to their breaking. Further, the requisite volume for a perfusion or an injection becoming smaller, it will be possible to use prefilled syringes of available sizes on the market, what will avoid all decant manipulation that have to be done in aseptic conditions in the hospital pharmacy. The adjunction of a device activating the piston of the syringe such as a push syringe, will allow the control at will of the flow during the perfusion. An other advantage is that it will be possible to provide such preparations in multidoses containers containing a bigger amount of doses and allowing the practitioner to remove at will the desired volume of the pharmaceutical oxiplatinum preparation without throwing the residual part of the non used preparation.

Another goal of the present invention is to make available a pharmaceutical oxaliplatinum preparation for parenteral administration at high concentration, which is stable during a pharmaceutically acceptable duration, i.e. which stays clear, colorless and free of precipitate at temperatures between 2–30° C. that can be met during transport, storage and/or manipulation.

With this end in view, it has been surprisingly found that the oxaliplatinum concentration and its stability at a wide range of utilization temperatures has been improved in a important way due to the presence in a pharmaceutical oxaliplatinum preparation of a very limited number of hydroxylated derivatives whose use is generally accepted for the preparation of medicaments.

Thus, one of the objects of the present invention is a pharmaceutically stable oxaliplatinum preparation for parenteral administration, the oxaliplatinum being contained in a solution in a solvent at a concentration of at least 7 mg/ml and the solvent comprising a sufficient quantity of at least one hydroxylated derivative chosen among 1,2-propanediol, glycerol, maltitol, saccharose and inositol. Preferably, the oxaliplatinum is contained in a solution in a solvent at a concentration of at least 7,5 mg/ml.

By a stable pharmaceutical oxaliplatinum preparation for parenteral administration it is meant a liquid preparation meeting the criterion generally fixed by the health authorities in order to be likely to be administered parenterally to the mammal.

Among these respected criterion, this preparation is clear, colorless and free of precipitate and stays like this for a pharmaceutically acceptable duration of at least six months, this duration extending to at least three years when the preparation is manipulated and/or preserved at temperatures which can vary between about 2° C. and about 30° C.

The limited choice of hydroxylated derivatives to use has been done following a very large number of tests of substances usually known to improve the solubility of medicinal substances in an aqueous medium. Some of these tests will appear in the examples as comparatives. For example, alcohols like ethanol and benzyl alcohol, dimethylformamid or dimethylacetamid did not allow, mixed with water, to considerably enhance the solubility of oxaliplatinum. Among the polyalkenes and in particular the polyalkene glycols having a molecular weight between 150 and 6000, only polyethylene glycol allows to enhance considerably the oxaliplatinum solubility. This compound has nevertheless not been retained as possible solvent component because the obtained solution was strongly colored. The crown ethers as some cyclodextrines allowed to enhance very slightly the oxaliplatinum concentration but not sufficiently for the desired applications. Among the carbon hydrates solubilised in water, lactose, sorbitol, solketal, mannitol, amongst others, have shown to be ineffective. Other carbohydrates such as cellobiose, trehalose, melibiose, gentiobiose, raffinose, stachyose or melozitose have shown that, solubilised in water, they allow to dissolve, at least a part of the oxaliplatinum but they are available on the market at a prohibitive price to be used as solvents. A wide range of surfactants, in particular Tween 20, Tween 60 and Tween 80 have shown to be ineffective to make oxaliplatinum soluble.

Preferably, in the pharmaceutical preparation according to the invention, oxaliplatinum is in solution at a concentration of at least 9 mg/ml. In this case, one milliliter of solvent comprises at least 100 mg of one or several hydroxylated derivatives chosen among 1,2-propane-diol, glycerol, maltitol, saccharose and inositol. When the hydroxylated derivatives are liquid at room temperature, then the solvent can be constituted 100% of at least one of these liquid derivatives. Generally the solvent comprises water too. The water used is preferably water as defined in the European Pharmacopea as being water for injectable preparations.

More preferably, the oxaliplatinum is contained in a solution in a solvent at a concentration comprised between about 10 mg/ml and about 15 mg/ml.

Besides, the solvent of the preparation according to the invention can include other compounds, excipients, adjuvants or additives usually recommended by the European Pharmacopea in the preparation of pharmaceutical parenteral preparations, except in particular all compound, metallic complex or salt, likely to degrade chemically oxaliplatinum. This is the case for compounds, metallic complexes generating, in particular in contact with water, chloride ions, or salts comprising chloride ions such as sodium chloride usually used to ensure isotony.

Thus, it is possible to use a buffer to control the pH of the preparation and/or strengthen the stability of oxaliplatinum. However, this use has not shown to be essential. If such a buffer is used, it has to be a buffer comprising at least one of the ligands of the oxaliplatinum metallic complex or the precursors of this ligand, for example a buffer based in particular on oxalic acid or on one of its salts such as sodium oxalate, preferably sodium oxalate.

It is also possible, to ensure the isotony to the blood of the preparation, to use, for example, an appropriate quantity of glucose.

It is also possible, to ensure a antimicrobial activity, to use antimicrobial preservatives. However this use has not shown to be essential because oxaliplatinum in solution has shown itself an antimicrobial efficacy in a test of artificial contamination recommended by the Pharmacopea.

Preferably, the pharmaceutical oxaliplatinum preparation according to the invention is packed in a container which can be closed or which is hermetic, appropriated for parenteral administration. Such a container can for example be a multidoses flask, a prefilled syringe, a soft perfusion bag or an ampoule.

The multidoses flask is generally equipped with a septum top allowing the passage of a syringe needle and contains a quantity of the preparation according to the invention that can be removed at will, sufficient to allow a certain number of perfusions or injections. For example, a multidoses container of 500 ml containing the preparation according to the invention, in which the oxaliplatinum is contained at a concentration of 10 mg/ml, contains a sufficient quantity of preparation to allow about twenty perfusions or injections. As mentioned above, the preparation according to the invention has shown in itself antimicrobial properties so that no adjunction of preservatives is needed.

The prefilled syringe presents the advantage that no decantation of the preparation according to the invention at room atmosphere is needed, thus it is not necessary to prepare the injection and/or perfusion equipment in aseptic conditions in the hospital pharmacy which is sometimes distant from the treatment room. The maximum volume of the prefilled syringes that are available on the market is generally 50 ml. As mentioned below, the preparation known in the prior art has a too low oxaliplatinum concentration to permit the use of one single prefilled syringe of 50 ml during one same perfusion. For example, the quantity of the preparation according to the invention having an oxaliplatinum concentration of 10 mg/ml necessary for a short perfusion treatment can be contained in a prefilled syringe of 25 ml. With such a prefilled 25 ml syringe, it is then also possible to use for example a push-syringe at programmable speed permitting in this way to control in a reliable manner the flow during the perfusion or injection, what lightens the supervision work of the practitioner.

One of the other objects of the present invention is the use, for the manipulation and/or storage and/or administration of the pharmaceutical preparation, of a multidoses container, a prefilled syringe, a soft perfusion bag or an ampoule.

Another object of the present invention is a method for making a pharmaceutical oxaliplatinum preparation as mentioned above, comprising a step of making oxaliplatinum soluble with a solvent comprising a sufficient quantity of at least one hydroxylated derivative chosen among 1,2-propane-diol, glycerol, maltitol, saccharose and inositol.

More precisely, this step comprises the following steps:
a) put in contact at a temperature inferior to 80° C. a quantity of oxaliplatinum with a sufficient quantity of said solvent to obtain an oxaliplatinum concentration of at least 7 mg/ml;
b) establish the mixture obtained at the step a) at a temperature comprised between 15–30° C.;
c) submit the mixture obtained at the step b) to a step of sterilization; and
d) the conservation in an adapted container as mentioned above for a parenteral administration of the mixture obtained at the step c) at a temperature comprised between 2–30° C.

Preferably, step a) is done at a temperature comprised between 20–60° C. More preferably, it is done at a temperature comprised between 30–60° C. The sterilization step according to step c) is done according to the usual methods well known by the specialist.

The pharmaceutical preparations according to the invention that are particularly interesting, their preparation, their advantages and in particular their embodiments are described in the following examples.

EXAMPLE 1

Making of the Pharmaceutical Preparations and Solubility Tests at a Concentration of 10 mg/ml The choice of the compounds likely to be comprised in the solvent of the preparation according to the invention has been done after visual observation of a clear colorless solution containing 10 mg oxaliplatinum per ml of the respective solvents after two periods of agitation of 24 hours at 25° C.

For every observed mixture the following visual classifications have been attributed:
- insoluble (I): the solid initial quantity of oxaliplatinum is practically stayed unchanged;
- partially soluble (PS): the solid initial quantity of oxaliplatinum has significantly diminished; and
- soluble (S): the solid initial quantity of oxaliplatinum has entirely or almost entirely been dissolved.

The apparition of a coloration (C) has also been observed.

A powder of oxaliplatinum (250 mg) is placed in a 50 ml container gauged at 25 ml. The compound to select (quantity mentioned in table 1) is introduced into the container jointly or prior to the adjunction of water completing ad 25 ml.

TABLE 1

| No of the mixture | 1.1 | 1.2 | 1.3 | 1.4 | 1.5 | 1.6 | 1.7 | 1.8 | 1.9 | 1.10 | 1.11 | 1.12 |
|---|---|---|---|---|---|---|---|---|---|---|---|---|
| Compound | ethanol | 1,2-propanediol | glycerol | lactose | maltitol | sorbitol | saccharose | inositol | PEG 200 | PEG 300 | Tween 20 | Tween 80 |
| Quantity | 9.8 g (12.5 ml) | 12.95 g (12.5 ml) | 15.76 g (12.5 ml) | 1.25 g | 5 g | 10 g | 2.5 g | 2.5 g | 14 g (12.5 ml) | 14 g (12.5 ml) | 27.4 g (25 ml) | 26.6 g (25 ml) |
| Solubility | PS | S | S | PS | S | PS | S | S | S | PS | PS | PS |
| Coloration | — | — | — | — | — | — | — | — | C yellowish | C yellowish | C | C |

From the observations recorded in table 1, it stands out that, at 25° C. under two agitations of 24 hours each, 250 mg oxaliplatinum in 250 ml of the mixtures No. 1.2, 1.3, 1.5, 1.7 and 1.8 appear to be soluble and that the obtained solutions are colorless. These mixtures are constituted of water and respectively of 1,2-propanediol, glycerol, maltitol, saccharose and inositol.

In the other mentioned mixtures, it is either soluble but in this case leads to yellowish colored solutions, either partially soluble. The numerous other compounds constituting mixtures in which the oxaliplatinum was insoluble, or very partially soluble, have not been registered in this table.

EXAMPLE 2

Optimization of the Solvent Composition for a Concentration of 10 mg/ml

An optimization of the quantity of the compounds likely to be comprised in the solvent of the preparation according to the invention has been done after visual observation of a clear colorless solution containing 10 mg oxaliplatinum per ml of the respective solvents after two agitation periods of 24 hours at 25° C., in a similar way to example 1 with this time again 250 mg oxaliplatinum in a 50 ml container gauged at 25 ml and completed ad 25 ml with the respective solvent.

Table 2 records, for the hydroxylated compounds 1,2-propanediol, glycerol and maltitol, the mixtures in which no residue is detected and the mixtures in which the first residues appear.

TABLE 2

| No of the mixture | 2.1 | 2.2 | 2.3 | 2.4 | 2.5 | 2.6 |
|---|---|---|---|---|---|---|
| Compound | 1,2-propanediol | 1,2-propanediol | glycerol | glycerol | maltitol | maltitol |
| Quantity | 5.9 g (7.5 ml) | 3.9 g (5.0 ml) | 6.3 g (5.0 ml) | 3.1 g (2.5 ml) | 5 g | 0.5 g |
| Solubility | S | PS | S | PS | S | PS |

EXAMPLE 3

Optimization of the Solvent Composition for a Concentration Higher than 10 mg/ml An optimization of the quantity of the hydroxylated compounds comprised in the solvent of the preparation according to the invention has been done after visual observation of a clear colorless solution by progressive increase of both the oxaliplatinum quantity and the hydroxylated compound quantity at constant solvent volume, always following the protocol described in Example 1.

Thus, for a volume completed ad 25 ml, an aqueous mixture containing 337,5 mg oxaliplatinum and 5 g maltitol is clear. On the other hand, residues appear in an aqueous mixture comprising 400 mg oxaliplatinum and 12,5 g maltitol.

The sample containing the 337,5 mg oxaliplatinum and the 5 g maltitol has been submitted to temperature variations which could be qualified as extreme. First it has been carried to 60° C. and maintained at this temperature under agitation during one hour. The solution obtained was clear and colorless. It was then submitted to three successive freezing with, in the interval, return to the room temperature. This solution has then staid seven days in a fridge. After this treatment, after return to room temperature, no crystal has been observed.

In 25 ml glycerol to 85%, it has been possible to partly dissolve 379,7 mg oxaliplatinum.

EXAMPLE 4

Determination of the Maximal Solubility of Oxaliplatinum at Room Temperature (21±2° C.) and at Fridge Temperature (5±3° C.).

To carry out this determination, five solvents have been prepared. They show the following compositions:
- solvent 4.1: 1,2-propanediol (50 ml) and water (50 ml);
- solvent 4.2: glycerol to 85% (50 ml) and water (50 ml);
- solvent 4.3: glycerol to 85% (40 ml) and water (60 ml);

solvent 4.4:1,2-propanediol (25 ml), glycerol (25 ml) and water (50 ml); and solvent 4.5: maltitol (50 g) and water (100 ml).

For every mixture to examine, the oxaliplatinum (1 g) and the considered solvent (50 ml) are introduced in a 100 ml Erlenmeyer. The mixture is placed in steam room at a temperature of 40° C. and is submitted to an agitation during 120 minutes. Sample removals are carried out respectively at 90 minutes and at 120 minutes. A part of these samples are brought to room temperature (21±2° C.). A visual control is carried out and the samples are then filtered. The amount of oxaliplatinum (mg/ml) is analyzed quantitatively by chromatography HPLC according to well established parameters. All results are recorded in table 4.

TABLE 4

| No. mixture | Aspect | Content oxaliplatinum (mg/ml), $T_{90\ min}$, 21 ± 2° C. | Content oxaliplatinum (mg/ml), $T_{120\ min}$, 21 ± 2° C. |
| --- | --- | --- | --- |
| 4.1 | colorless | 14.01 | 14.33 |
| 4.2 | colorless | 13.59 | 13.68 |
| 4.3 | colorless | 12.77 | 12.93 |
| 4.4 | colorless | 13.74 | 13.70 |
| 4.5 | colorless | 13.04 | 13.14 |

Another part of the samples containing the mixture 4.5 with solvent 4.5 are placed in a fridge at a temperature of 5±3° C. and left at this temperature during seven days. A visual control is done, then the samples are cold filtered. The content of oxaliplatinum (mg/ml) is quantitatively analyzed by chromatography HPLC according to well established parameters. The measured oxaliplatinum content is of 12,84 mg/ml and the solution is colorless.

EXAMPLE 5

Stability Control Over 3 Months

To carry out this control, the oxaliplatinum has been dissolved 10 mg/ml in respective the four solvents of the following compositions:

solvent 5.1:1,2-propanediol (50 ml) and water PPI (50 ml);

solvent 5.2: glycerol to 85% (50 ml) and water PPI (50 ml);

solvent 5.4:1,2-propanediol (25 ml), glycerol (25 ml) and water PPI (50 ml); and solvent 5.5: maltitol (50 g) and water PPI (100 ml);

with the expression "water PPI" meaning Water for injectable preparations in the sense of the European Pharmacopea.

The obtained preparations, split in a certain number of shares, have been sterilized according to usual methods known by the specialist. These shares have been preserved sheltered from light during three months, a first part at a temperature of about 25° C. at a relative humidity level of 60%, a second part at a temperature of about 40° C. and a relative humidity level of 75% and at last a third part at a temperature of about 4° C. Removals have been carried out at time 0, 1 month and at 3 months, and have been submitted to a certain number of physico-chemical analyses. The obtained results have shown that the four preparations are stable for at least 3 months.

EXAMPLE 6

Efficacy of the Antimicrobial Conservation

This study has been carried out by the method recommended at section 5.1.3. of the European Pharmacopea having for title "Efficacy of the antimicrobial conservation" exposing an oxaliplatinum preparation to the stump *Staphylococcus aureus*. Under these conditions, the obtained results have shown a definite reduction of the *staphylococcus aureus* population with a Δlog of 5,99 after 24 hours.

The invention claimed is:

1. Oxaliplatinum stable pharmaceutical preparation for parenteral administration, characterized in that the oxaliplatinum is contained in a solution in a solvent at a concentration of at least 7 mg/ml and in that said solvent comprises a sufficient quantity of a hydroxylated derivative selected among 1,2-propanediol, glycerol, maltitol, saccharose and inositol.

2. Pharmaceutical preparation according to claim 1, characterized in that the oxaliplatinum is contained in a solution in said solvent at a concentration of at least 9 mg/ml and in that 1 ml of said solvent comprises at least 100 mg of one or several of said hydroxylated derivatives.

3. Pharmaceutical preparation according to claim 2, characterized in that said solvent further comprises water.

4. Pharmaceutical preparation according to claim 3, characterized in that the oxaliplatinum is contained in a solution in said solvent at a concentration comprised between about 10 mg/ml and about 15 mg/ml.

5. Pharmaceutical preparation according to claim 1, characterized in that it is packed in an appropriate container for parenteral administration.

6. Pharmaceutical preparation according to claim 5, characterized in that said container is a multidoses flask.

7. Pharmaceutical preparation according to claim 5, characterized in that said container is a prefilled syringe.

8. Pharmaceutical preparation according to claim 5, characterized in that said container is a soft perfusion bag.

9. Pharmaceutical preparation according to claim 5, characterized in that said container is an ampoule.

10. Method for the preparation of a pharmaceutical preparation according to claim 1 comprising a step of mixing oxaliplatinum with a solvent comprising a sufficient quantity of at least one hydroxylated derivative selected among 1,2-propanediol, glycerol, maltitol, saccharose and inositol.

11. Method according to claim 10, characterized in that it comprises the following steps:
  a) put in contact at a temperature less than 80° C. a quantity of oxaliplatinum with a sufficient quantity of the said solvent to obtain an oxaliplatinum concentration of at least 7 mg/ml;
  b) establish the mixture obtained at the step a) at a temperature comprised between 15–30° C.;
  c) submit the mixture obtained at the step b) to an aseptic filtration; and
  d) the conservation in an adapted container for a parenteral administration of the mixture obtained at the step c) at a temperature comprised between 2–30° C.

12. A multidoses flask containing the pharmaceutical preparation according to claim 1.

13. A prefilled syringe containing the pharmaceutical preparation according to claim 1.

14. A soft perfusion bag containing the pharmaceutical preparation according to claim 1.

* * * * *